United States Patent [19]

Ornitz

[11] Patent Number: 5,891,655
[45] Date of Patent: Apr. 6, 1999

[54] METHOD OF IDENTIFYING MOLECULES THAT REGULATE FGF ACTIVITY

[75] Inventor: David M. Ornitz, St. Louis, Mo.

[73] Assignee: Washington University, St. Louis, Mo.

[21] Appl. No.: 839,186

[22] Filed: Apr. 23, 1997

Related U.S. Application Data

[62] Division of Ser. No. 404,655, Mar. 15, 1995, Pat. No. 5,733,893.

[51] Int. Cl.[6] .................................................. G01N 33/567
[52] U.S. Cl. ........................ 435/7.21; 435/69.1; 435/69.4; 435/172.3; 424/1.73; 424/158.1; 530/399; 536/1.1; 536/4.1; 536/21; 536/123; 536/123.13
[58] Field of Search ............................... 435/240.2, 69.1, 435/7.21, 172.3, 69.4; 530/399; 424/1.73, 158.1; 536/1.1, 4.1, 21, 123, 123.13

[56] References Cited

U.S. PATENT DOCUMENTS 5,155,214  10/1992  Baird et al. .............................. 536/399
5,270,197  12/1993  Yayon et al. .......................... 435/240.2

FOREIGN PATENT DOCUMENTS

WO-93/19096  9/1993  WIPO .............................. C08B 37/10

OTHER PUBLICATIONS

Klagsbrun & Baird, Cell, 67, 229–231, (Oct. 18, 1991).
Ornitz et al., Mol. Cell. Biol., 12, 240–247, (Jan., 1994).
Yayon et al., Cell, 64, 841–848 (Feb. 22, 1991).
Kan, et al., Science, 259, 1918–1921 (Mar. 26, 1993).
Ishihara et al., J. Biol. Chem., 268, 4675–4683 (March 5, 1993).
Westman et al., J. Carbohyd. Chem. 14, 95–113 (1995). Month not available.
Eriksson et al., Proc. Natl. Acad. Sci. USA 88, 3441–45 (Apr. 1991).
Chellalah et al., J. Biol. Chem., 269, 11620–27 (Apr. 15, 1994).
Ornitz et al., J. Cellular Biol. vol. O, No. 19A, 5–26 Jan. 1995, p. 25.
Tyrell et al., J. Biol. Chem. vol. 268, No. 7, Mar. 5,1993, pp. 4684–4689.
Ishibara et al., Glycobiology, vol. 4, No. 6, Dec. 1994, pp. 432–436.
Ornitz et al., Science, vol. 268, Apr. 21, 1995, pp. 432–436.
Venkataraman et al., Proc. Natl. Acad. Sci. USA, vol. 93, Jan. 1996, pp. 845–850.

*Primary Examiner*—James O. Wilson
*Attorney, Agent, or Firm*—Scott J. Meyer

[57] ABSTRACT

Disclosed are fibroblast growth factor (FGF) binding and FGF receptor activation, and a method of identifying small molecular weight compounds that interact with FGF to modulate its activity such as, e.g., activators and inhibitors. Illustrative small oligosaccharides, namely di- and tri-saccharides, are shown to be effective modulators of FGF binding and FGF receptor activation.

5 Claims, 10 Drawing Sheets

METHOD OF IDENTIFYING MOLECULES THAT REGULATE FGF ACTIVITY

This is a Division, of application Ser. No. 08/404,655, filed Mar. 15, 1995 now U.S. Pat. No. 5,733,893.

This invention was made in part with government support under Grant Number CA 60673 awarded by the National Institutes of Health. The government has certain rights in the invention.

BACKGROUND OF THE INVENTION

The present invention relates to fibroblast growth factor (FGF) binding and FGF receptor (FGFR) activation. More particularly, the invention relates to a method of identifying compounds that interact with FGF and modulate its activity such as, for example, activators and inhibitors.

(Note: Literature references on the following background information and on conventional test methods and laboratory procedures well known to the ordinary person skilled in the art, and such other state-of-the-art techniques as used herein, are indicated in parentheses and appended at the end of the specification.)

FGFs regulate a diverse range of physiologic processes such as cell growth and differentiation and pathologic processes involving angiogenesis, wound healing and cancer (1).

FGFs utilize a dual receptor system to activate signal transduction pathways (2–5). The primary component of this system is a family of signal-transducing FGF receptors (FGFRs) that contain an extracellular ligand-binding domain and an intracellular tyrosine kinase domain (1).

The second component of this receptor system consists of heparan sulfate (HS) proteoglycans or related heparin-like molecules which are required in order for FGF to bind to and activate the FGFR (3,4).

Heparin/HS may interact directly with the FGFR linking it to FGF (6). Furthermore, heparin/HS can facilitate the oligomerization of two or more FGF molecules, which may be important for receptor dimerization and activation (3). There are no pharmacologic agents that were previously known to modulate the activity of FGFs.

Heparin/HS is a heterogeneously sulfated glycosaminoglycan that consists of a repeating disaccharide unit of hexuronic acid and D-glucosamine. It has been previously reported that, at a minimum, highly sulfated octa- (3) or decasaccharide (7) fragments derived from heparin are required for FGF to bind to the FGFR. However, preparation of these heparin fragments produces mixtures of isomers and chemically modifies the oligosaccharide ends (8). Furthermore, size-fractionated heparin may contain individual molecules with distinct biological properties.

Accordingly, it would be desirable to determine the mechanism by which heparin/HS activates FGF and, further, to identify compounds that interact with FGF and modulate its activity.

In U. S. Pat. No. 5,270,197, various systems are described for assaying the ability of a substance to bind to a high-affinity heparin-binding growth factor (HBGF) receptor, e.g. an FGF receptor. The disclosure of said patent is incorporated herein by reference.

BRIEF DESCRIPTION OF THE INVENTION

In accordance with the present invention, a method is provided for modulating the activity of heparin/HS-dependent mitogenesis which comprises subjecting a biological fluid which contains FGF to a mitogenesis-modulating amount of a small oligosaccharide having from 2 to about 6 saccharide units.

The biological fluid can be any fluid which contains or is compatible with the FGF, e.g., an aqueous solution of FGF, conditioned cell culture medium, serum or plasma, or a physiologically acceptable solution of the FGF. Agents that modulate the activity of FGF are useful in wound healing, angiogenesis and cancer treatment.

According to another embodiment of the invention, a method is provided for identifying a compound that interacts with FGF to thereby modulate its activity comprising subjecting said compound to one or more of the following assay procedures:

(a) testing the ability of the compound as a modulator of FGF-dependent mitogenesis on FGF receptor-expressing cells and comparing against the mitogenic activity of heparin or sucrose octasulfate;

(b) testing the ability of the compound to compete with the binding of $^{125}$I-heparin to FGF;

(c) testing the ability of the compound to enhance or inhibit the binding of FGF to a soluble or cell surface FGF receptor;

(d) testing the ability of the compound to enhance or inhibit FGF dimerization;

(e) testing the ability of the compound to enhance or inhibit FGF receptor dimerization; and (f) testing the ability of the compound to enhance or inhibit FGF binding to heparin or heparin immobilized on a gel matrix.

The gel matrix for the heparin immobilization can be, e.g., an agarose such as SEPHAROSE®.

Compounds that can thus be identified as modulators of FGF activity are, e.g., organic compounds, compounds that contain carbohydrate moieties such as oligosaccharides and polysaccharides and compounds containing heparin-like structures. These compounds preferably are small molecular weight compounds of up to about 1000 Daltons.

Initially, to determine the molecular mechanism by which heparin/heparan sulfate (HS) activates FGF, small non-sulfated oligosaccharides found within heparin/HS were assayed for activity. These oligosaccharides are di- and tri-saccharides which are synthetic and isomerically pure compounds and do not contain any modified sugar residues (9). The chemical structures of illustrative small oligosaccharides are set forth in Table 1, below.

TABLE 1

Heparin/HS oligosaccharides.

| Name | Mw | Structure# |
|---|---|---|
| Di-1 | 433.3 | α-L-IdoA-(1→4)-α-D-GlcNAc-1→OMe |
| Di-2 | 493.2 | α-L-IdoA-(1→4)-α-D-GlcNSO$_3$-1→OMe |
| Di-3 | 433.3 | β-D-GlcA-(1→4)-α-D-GlcNAc-1→OMe |
| Di-4 | 493.2 | β-D-GlcA-(1→4)-α-D-GlcNSO$_3$-1→OMe |
| Di-5 | 433.3 | α-D-GlcNAc-(1→4)-β-D-GlcA-1→OMe |
| Tri-1 | 631.4 | β-D-GlcA-(1→4)-α-D-GlcNAc-(1→4)-β-D-GlcA-1→OMe |
| Tri-2 | 691.2 | α-L-IdoA-(1→4)-α-D-GlcNSO$_3$-(1→4)-β-D-GlcA-1→OMe |
| Tri-3 | 631.4 | α-L-IdoA-(1→4)-α-D-GlcNAc-(1→4)-β-D-GlcA-1→OMe |

IdoA, iduronic acid; GlcA, glucuronic acid; GlcN, glucosamine; Gal, galactose; aManOH, 2-5-anhydro-D-mannitol; Ac, acetate; Me, methyl;

The most preferred of these small oligosaccharides are Tri-1 and Tri-3. They are active at concentrations comparable to heparin and are 1000-fold more active than sucrose octasulfate (SOS) in an assay which measures the proliferation of FGFR-expressing BaF3 cells (3) in the presence of basic FGF (bFGF). Four disaccharides, Di-2, 3, 4 and 5, show intermediate mitogenic activity with bFGF, with D-3 and D-4 being the most active of the disaccharides.

The most preferred small oligosaccharides, Tri-1 and Tri-3, also stimulate the proliferation of FGFR-expressing BaF3 cells in the presence of acidic FGF (aFGF).

These results with small oligosaccharides having from 2 to about 6 saccharide units were unexpected since they are considerably smaller than the smallest heparin/HS oligosaccharides previously shown to activate FGF, namely octa- (3) and decasaccharides (7).

DETAILED DESCRIPTION OF THE INVENTION

While the specification concludes with claims particularly pointing out and specifically claiming the subject matter regarded as forming the present invention, it is believed that the invention will be better understood from the following detailed description of preferred embodiments of the invention taken in conjunction with the appended drawings.

BRIEF DESCRIPTION OF THE DRAWINGS

FIG. 1 is a graphical representation which shows the mitogenic activity of synthetic oligosaccharides. Activation of bFGF mitogenic activity as measured by $^3$H-thymidine incorporation into FGFR1-expressing BaF3 cells treated with 150 pM bFGF and increasing concentrations of the indicated oligosaccharides is shown. Inset: Activation of aFGF mitogenic activity determined as above in the presence of 250 pM aFGF; these data are representative of at least two independent experiments.

FIG. 2, in four parts, FIGS. 2A, 2B, 2C AND 2D, is a graphical representation which shows the biochemical properties of synthetic oligosaccharides.

The $IC_{50}$s (50% competition for $^{125}$I-heparin binding to bFGF are: 69 ng/ml for heparin, 11.7 μg/ml for Tri-1, 5.8 μg/ml Tri-3 and 93 μg/ml for SOS (sucrose octasulfate).

FIG. 2D:, basic FGF binding to FRAP. $^{125}$I-FGFs were incubated with FRAP in the presence of increasing concentrations of heparin or Tri-3; Binding assays were performed as previously described (3).

FIG. 3, in four parts, FIGS. 3A, 3B, 3C and 3D, shows the crystal structure of bFGF complexed with synthetic oligosaccharides.

Thick lines indicate the ligand atoms. Thin lines indicate contour lines of electron density at 1.8σ above the mean density, in a map calculated using the coefficients $(2|Fo|-|Fc|)\exp(-i\alpha_c)$ where $|Fo|$ is the observed structure factor amplitude, and $|Fc|$ and $\alpha_c$ are the amplitudes and phases calculated from the model and adjusted by adding the structure factor of the solvent (14).

The label prime refers to symmetry-related molecules. β strands are shown as arrows. The notation used is according to (17) with strands labeled from β1 to β12 and loops labeled with the numbers of the secondary structures they join.

Only secondary structures participating in the Di-3/bFGF interaction are indicated. However, the location and features of the Tri-3 binding sites are essentially the same.

Tri-3 is shown with thick solid black bonds.

Sugar rings are labeled A, B, C, with A indicating iduronic acid, B, N-acetyl glucosamine, and C, O-methyl glucuronic acid.

Medium-thick and thin lines indicate amino acid atoms involved in site 1 and 1', respectively.

Dotted lines indicate hydrogen bonds.

Atoms and amino acids involved in hydrogen bonds are indicated by a prime label when the bond involves atoms of site 1'.

The oligosaccharide in site 1 is within a pocket of high positive potential that includes primarily amino acids of the 10–11 and 11–12 loops (see FIG. 3B for notation). Site 1' makes contacts with regions of the structure that include the 5–6 loop and the β4 strand.

Notation is as in FIG. 3C. Site 2 consists of regions of the structure that include the β8 strand and the 4–5 loop.

Site 2' consists of a largely hydrophobic platform (strands β6 and β7) flanked by positively charged residues Arg 72 and Lys 86 on one side and residues Arg 81 and Lys 77 on the other side.

FIG. 4 shows the bFGF dimerization in the presence of heparin hexadecasaccharide (HS-16) or synthetic oligosaccharide Tri-3. 670 nM bFGF and $3\times10^5$ cpm $^{125}$I-bFGF were incubated with the indicated concentration of (μg/ml) Tri-3 or HS-16. Crosslinking and electrophoresis were performed as previously described (3). Dimer (45 kD) band intensities were quantified by scanning densitometry and plotted above each lane. Molecular weight markers (kD) are shown at the right.

MoLTR is the Molony murine leukemia virus long terminal repeat;

mFGFR1 is the FGF receptor-1 open reading frame;

emc IRES is the internal ribosome entry sequence;

NeoR is the neomycin resistance gene;

SV40polyA is the late polyA addition site of the SV40 virus; and

BSSK(+) is the bluescript (pBS) SK (+) vector (Stratagene Inc.)

Restriction enzyme sites are shown on the periphery by their conventional abbreviations.

FIG. 6 shows the dimerization of FGF receptors induced by FGF-2 and heparin-trisaccharide (Tri-3). $^{125}$I-bFGF($2\times10^6$ cpm) was incubated with $4\times10^6$ BaF3 -FGFR1 cells. Binding media (DMEM/0.1% BSA) was supplemented with the indicated concentration of heparin or Tri-3. (*) 200 ng/ml unlabeled FGF-2 added to binding media; Cells were washed once with the same media used for binding, and once with PBS. Crosslinking was as described previously (27).

Crosslinked receptors were electrophoresed on a 5% SDS polyacrylamide gel under reducing condition, and visualized by autoradiography. The lower band corresponds to receptor monomers crosslinked to FGF-2. The upper band corresponds to receptor diners crosslinked to each other and to FGF-2. Molecular weights (kD) are shown at the right.

In order to illustrate the invention in further detail, the following specific laboratory examples were carried out with the results indicated. Although specific examples are thus illustrated, it will be understood that the invention is not limited to these specific examples or the details therein.

EXAMPLES

Materials and Methods

Basic fibroblast growth factor (bFGF) was obtained from Scios Nova. Acidic fibroblast growth factor (aFGF) was obtained from Merck & Co., Inc.

Heparin/HS-derived di- and tri-saccharides were obtained from Pharmacia AB.

FGFR3-expressing BaF3 cells have been described previously (27).

FGFR1-expressing BaF3 cells can be made by transfecting the expression plasmid MIRB-FR1 (FIG. 5) into BaF3 cells and selecting with the antibiotic G418 (geneticin) at about 600 $\mu$g/ml for 10 days and picking colonies.

Individual colonies are FGF- and heparin-dependent. The plasmid MIRB-FR1 (FIG. 5) is constructed analogously to previously published procedures (27) for preparing FGFR3 expression vectors (see FIG. 5A in Ref. 27), except that the FGFR1 gene is used instead of the FGFR3 gene.

Figure 5:
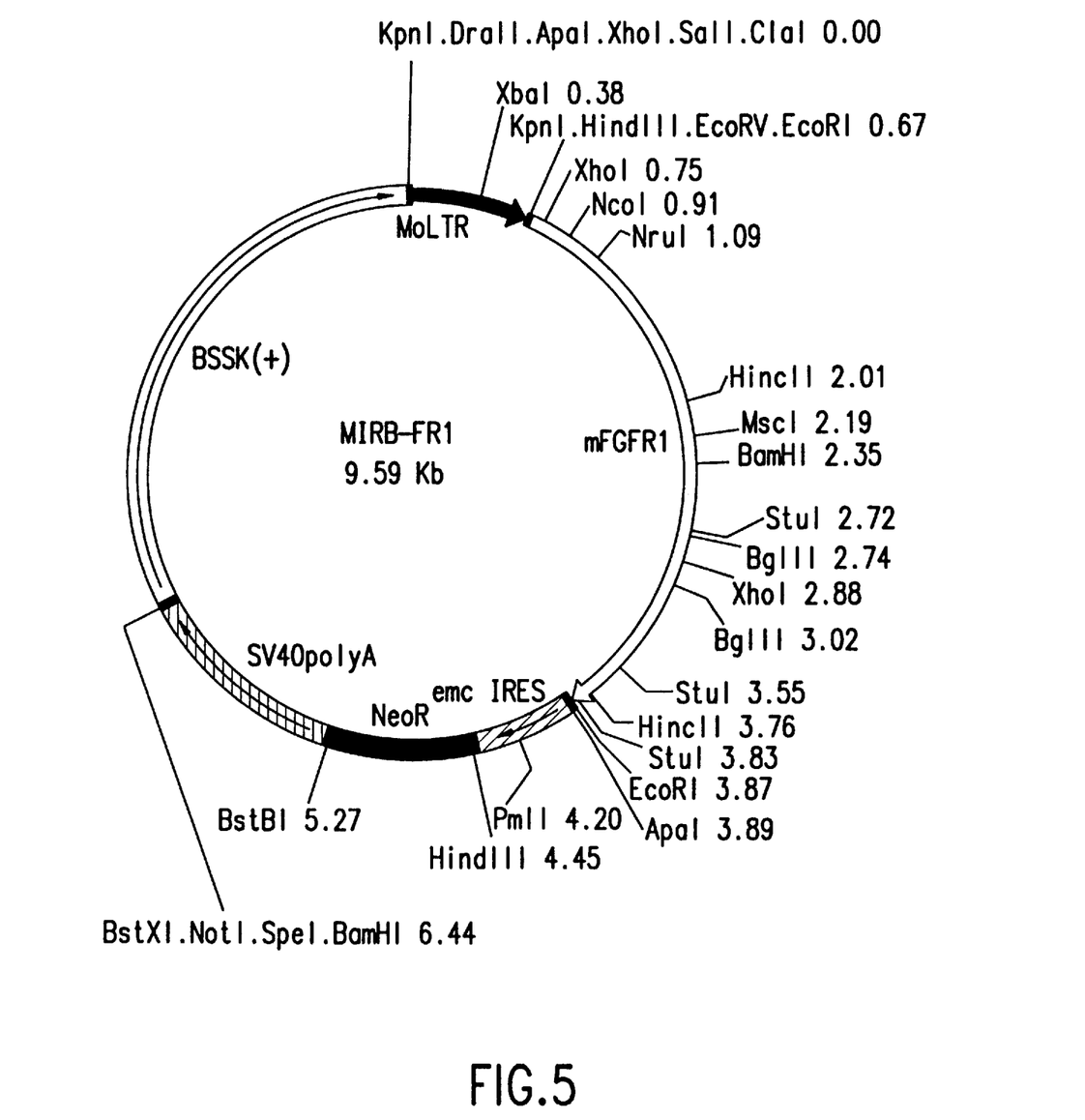
FIG. 5 is a schematic diagram of the restriction enzyme map of the plasmid MIRB-FR1, which is an 9.59 Kb expression vector for FGF receptor-1, a cell surface receptor. In this vector.

The relationship of the FGFR1 gene and the Molony murine leukemia virus long terminal repeat (LTR) is identical to that previously published (3). See also U.S. Pat. No. 5,270,197, FIG. 11A, for the construction of another suitable plasmid, namely mFR1, which contains the Molony virus LTR, and can be transfected into Ba3F cells and selected with G418.

The FGFR1-expressing BaF3 cell line was used to assay synthetic heparin/HS molecules as potential activators or inhibitors of heparin/HS-dependent mitogenesis by an assay procedure published previously (3). Such cell lines, which express FGFR-1, require heparin/HS and FGF for growth (3). The ability of heparin/HS-derived di- and tri-saccharides to enhance FGF-FRAP binding in vitro was measured by this assay.

The structures of di- and tri-saccharides which were thus assayed are shown in Table 1, above. Their synthesis was published previously (9).

The ability of these small oligosaccharides to compete with the binding on $^{125}$I-heparin to FGF was also assayed. Heparin iodination was carried out by previously published procedure (30). Heparin binding to FGF was determined by incubating 4 nM FGF with $^{125}$I-heparin and competitor polysaccharide. Complexes were immunoprecipitated with 1:250 dilutions of monoclonal antibody DG2 (DuPont/Merck) (for bFGF) or a polyclonal antibody (for aFGF), and protein A SEPHAROSE (Sigma Chemical Co.). Washing and quantitation was carried out by procedures previously published for soluble receptor-binding assays (3).

The crystal structure of complexes between bFGF and biologically active di- and trisaccharides was determined. Four binding sites were observed, sites 1, 1', 2 and 2'. Sites 2 and 2' have not been observed previously. The ability of these di- and trisaccharides to bind the 2/2' sites on bFGF may contribute to their biological activity.

Small crystals of complexes of bFGF (25 mg/ml) and Di-3 or Tri-3 (1 to 1.3 ratios) were obtained at 20° C. (33) in 15% or 17.5% (w/v), respectively, polyethylene glycol (average Mr=3350), 0.1M HEPES (pH 6.8), and subsequently macroseeded repeatedly in fresh drops of the same solution. Both complexes form triclinic crystals with one molecule in the asymmetric unit (a=30.9, b=33.3, c=34.7, $\alpha$=87.6, $\beta$=85.4, $\gamma$=76.4). Structure determination was carried out as in (34,35) with the model generated by (18).

The oriented model was then refined by simulated annealing and least-squares optimization, as in (37). Data from 40 Å to 2.2 Å were used.

Examination of a map generated using the coefficients (|Fo|−|Fc|)exp(−i$\alpha_c$) showed density that could accommodate saccharide molecules in both sites 1 and 2.

Subsequent incorporation of the structure factor of the solvent resulted in improved density. Model building and correction was carried out with the programs O (38,39) and turbo (40).

Least-squares refinement of the saccharide-FGF structure was carried out with X-PLOR (36), with stereochemical parameters for Di-3 and Tri-3 taken from the topology and parameter files provided for pyranoside sugars by the X-PLOR package (36).

The final R-factor is 22.0% and 22.8% for the Tri-3/bFGF and Di-3/bFGF structures, respectively, with good stereochemistry. Analysis of the temperature factors indicated that the occupancy of the saccharides is likely to be partial. Occupancy of the di- and trisaccharide was set to 0.5, which results in temperature factors that are comparable to those for side-chains observed to coordinate the ligands.

Results

The FGFR1-expressing BaF3 cell line, which expresses FGFR 1, requires heparin/HS and FGF for growth (3). This cell line was used to assay synthetic heparin/HS molecules as potential activators or inhibitors of heparin/HS-dependent mitogenesis (3).

Figure 1A:
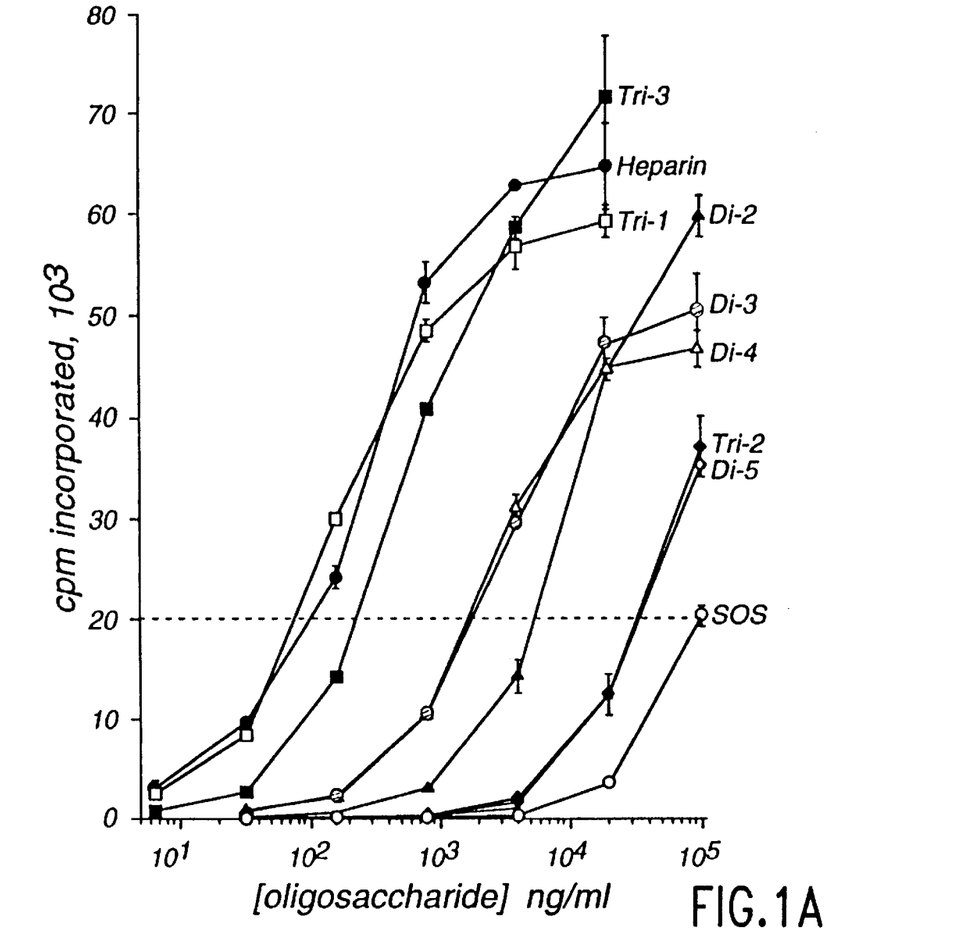
Figure 1B:
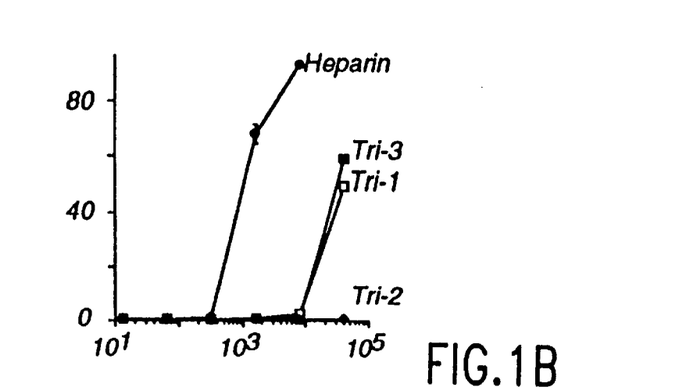

Two trisaccharides, Tri-1 and Tri-3, are active at concentrations comparable to that of heparin (FIG. 1, Table 2). The third trisaccharide, Tri-2 (containing a glucosamine N-sulfate), and four disaccharides, Di-2, 3, 4, and 5, show intermediate mitogenic activity with basic FGF (bFGF) whereas the disaccharide Di-1 and the three tetrasaccharides examined demonstrate no activity in this assay.

Sucrose octasulfate (SOS), a highly charged molecule thought to stabilize and activate bFGF (10), was also examined. Heparin, Tri-1, and Tri-3 are greater than 1000-fold more active than SOS for FGFR1-expressing BaF3 cell growth. Di-3 and 4 are 55-fold more active in this assay.

Unlike previously examined fragments of heparin, several of these synthetic heparin/HS molecules are non-sulfated, yet they still have biological activity. Furthermore, they are considerably smaller than the smallest heparin/HS oligosaccharide previously shown to activate FGF (3).

Because several of these oligosaccharides are non-sulfated, interactions with the carbohydrate backbone of heparin/HS appear to be sufficient for biological activity. Furthermore, the large differences in activity observed between closely related oligosaccharides suggest that these interactions are highly specific.

Two of the three trisaccharides (Tri-1 and Tri-3) stimulate proliferation of FGFR1-expressing BaF3 cells in the presence of aFGF. However, their potency relative to that of heparin is less than that observed with bFGF (FIG. 1 inset). These data demonstrate that the structure-function relationship between heparin/HS and aFGF is similar to that of bFGF and suggests that recognition of the structural features of heparin/HS is a conserved property of FGFs and not specific to a single ligand.

Figure 2A:
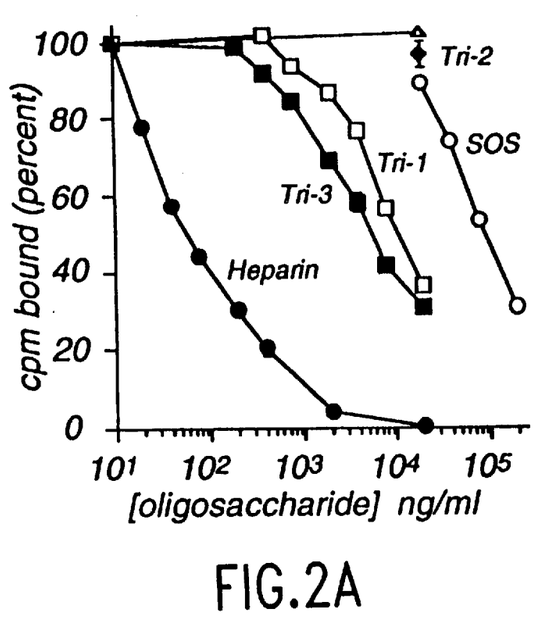
FIG. 2A: Binding of oligosaccharides to bFGF as determined by competition with $^{125}$I-heparin (30).

FGFs have a high affinity for heparin ($K_d$ $10^{-9}$M) (11). The ability of the synthetic oligosaccharides to compete with the binding of $^{125}$I-heparin to FGF was assayed (12). Heparin, oligosaccharides Di-3, Di-4, Tri-1, and Tri-3, and the related molecule, SOS, all bind aFGF and bFGF (FIG. 2A, Table 2) (9).

Heparin, Tri-1 and Tri-3 bind FGF with an affinity higher than that of SOS. Di-3, Di-4 and SOS bind FGF with similar affinity, whereas Di-2 and Tri-2 bind bFGF with an affinity less than that of SOS. The number of hydrogen bonds in the crystal structures of Di-3 and Tri-3 complexed with FGF (see below) correlate well with these data. The relative binding affinities also correlate well with the mitogenic activity of these molecules. However, on the basis of the relative affinities for bFGF (Table 2), Di-2, Tri-1, and Tri-3 show higher than expected mitogenic activity. Thus, factors other than direct binding to bFGF may contribute to the biological activity of these molecules.

Figure 2B:
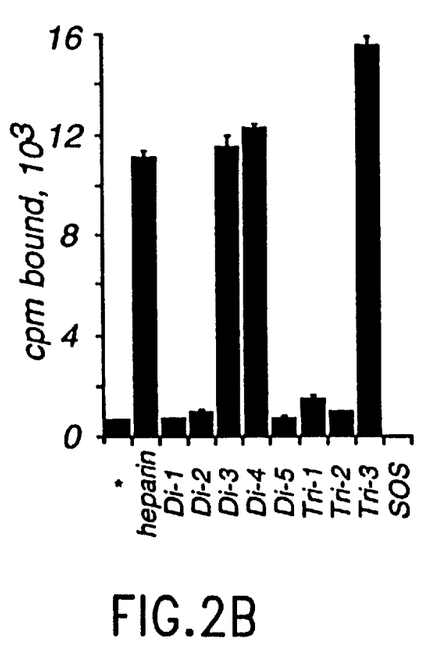
FIG. 2B: Binding of $^{125}$I-bFGF to FRAP (3), a soluble receptor, in the presence of the indicated oligosaccharide: *, no heparin added; heparin, 50 ng/ml; the remaining oligosaccharides (Di-1 to SOS) were added at a concentration of 2 μg/ml. FGFs were labeled by the Chloramine T method as previously described (31).

Binding of bFGF to a soluble FGFR-alkaline phosphatase fusion protein (FRAP) or to a cell-surface FGFR is enhanced by heparin/HS or by heparin-derived oligosaccharides (8 to 12 sugar residues) (3,4). The ability of heparin/HS-derived di- and tri-saccharides to enhance FGF-FRAP binding in vitro was measured (3). These studies demonstrate that Di-3, Di-4, and Tri-3 enhance bFGF-FRAP binding (FIG. 2B).

Figure 2C:
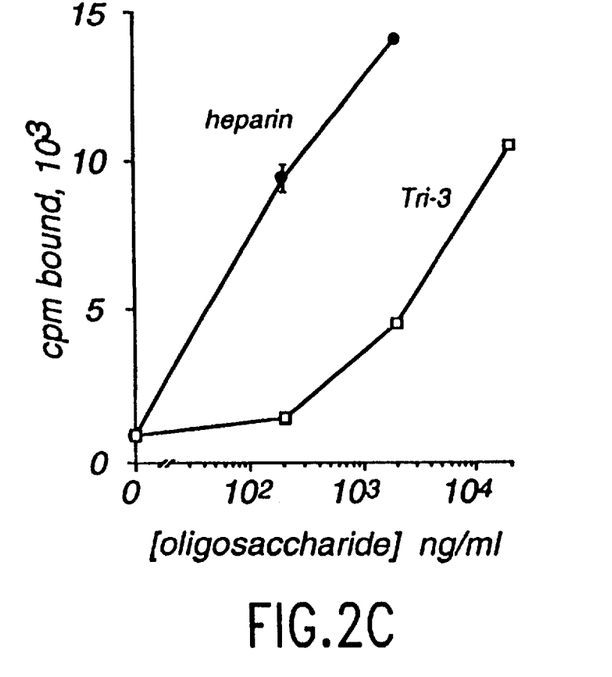
FIG. 2C: Acidic FGF binding to FRAP.
Figure 2D:
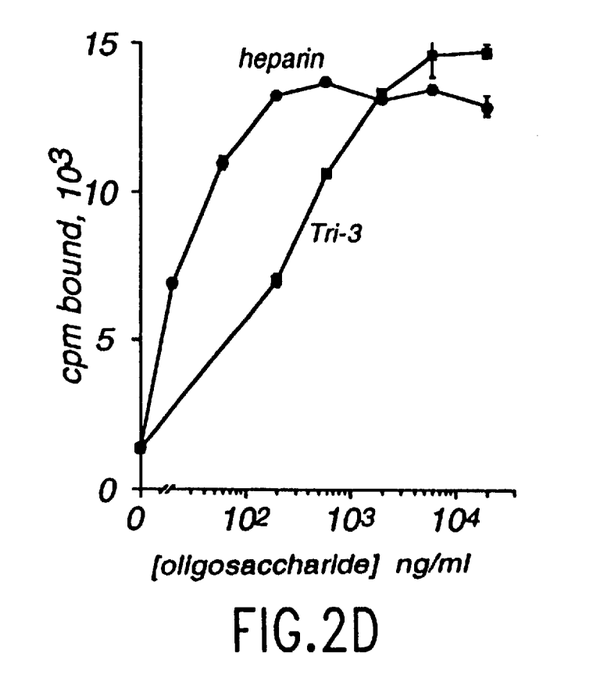

Furthermore, the binding of either aFGF (FIG. 2C) or bFGF (FIG. 2D) to FRAP increases in a dose-dependent manner. At high concentrations of Tri-3, the amount of $^{125}$I-bFGF bound to FRAP reproducibly exceeds that with heparin (FIG. 2D).

The observation that small di- and trisaccharides can enhance FGF-FRAP binding suggests that multiple binding sites along a single heparin/HS chain (beads on a string model) are not essential for biological activity, and that the occupancy of a relatively small heparin/HS binding site(s) on FGF may be sufficient to activate FGF.

The inability of Tri-1 to enhance FGF-FRAP binding suggests that several mechanisms may mediate FGF receptor activation. Clearly the substitution of iduronic acid for a glucuronic acid at the non-reducing end of the saccharide is sufficient to discriminate between different modes of action.

Heparin/HS may stabilize a ternary complex by binding directly to the FGFR (6) in addition to FGF. To investigate this model, FRAP was incubated with $^{125}$I-heparin (12). No significant binding (>2 fold over background) between $^{125}$I-heparin and FRAP could be detected. However, when bFGF (up to 4 nM) was added to this binding reaction, $^{125}$I-heparin binding was increased up to 25.5-fold over background (13). These data and the observation that molecules as small as disaccharides were biologically active suggest that the mechanism by which heparin/HS activates the FGFR results from a primary interaction between the FGFR and a complex of heparin/HS and FGF.

Figure 3A:
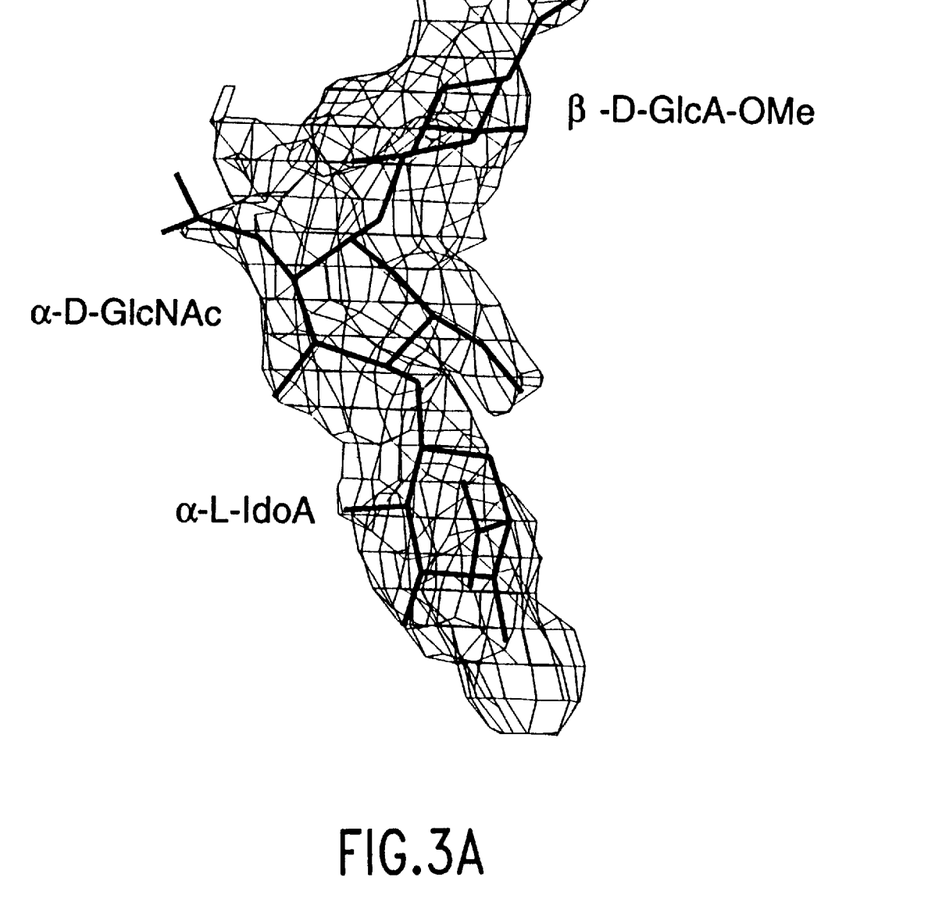
FIG. 3A: Electron density for Tri-3 ligand in sites 2/2' at 2.2 Å resolution.
Figure 3B:
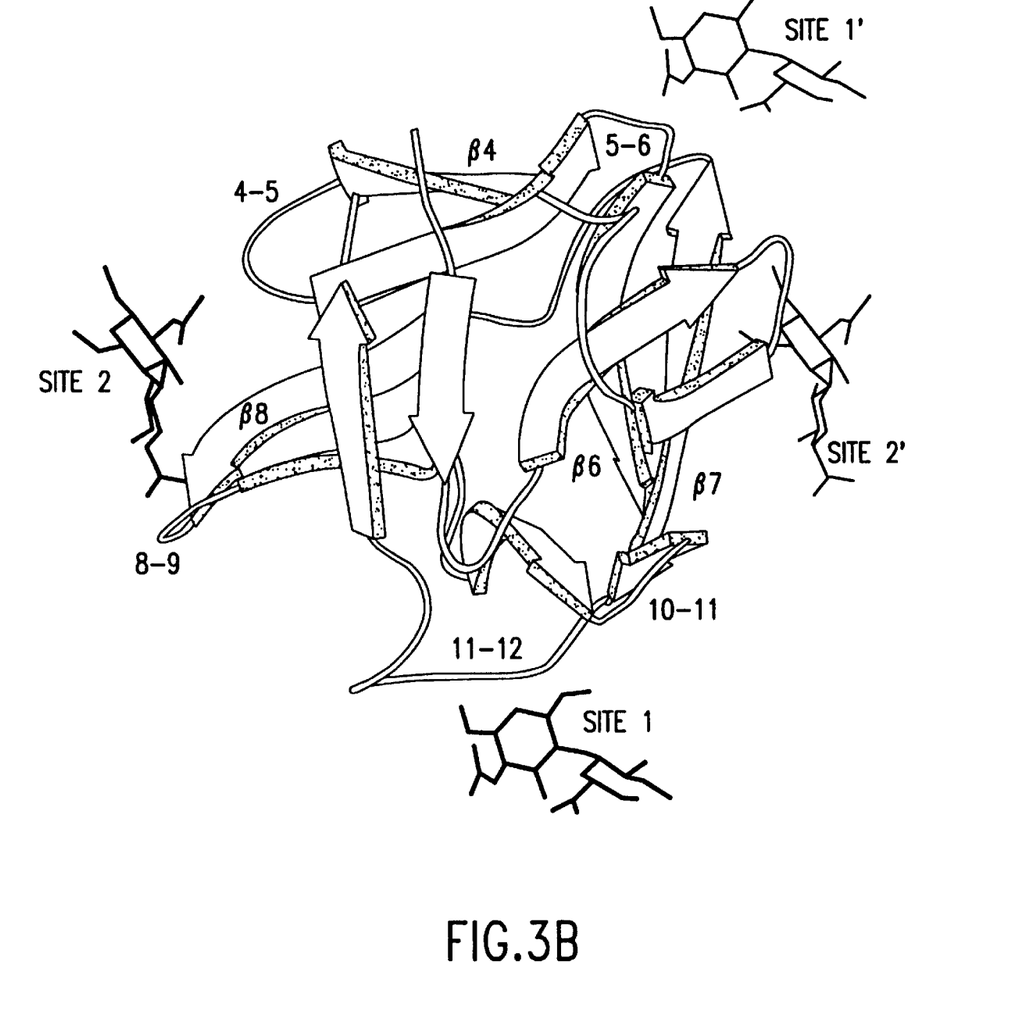
FIG. 3B: Ribbon diagram (32) of bFGF bound to Di-3 molecules, shown with solid black bonds and labeled according to the sites to which they bind.

To further evaluate the mechanism by which heparin/HS activates FGF and to establish a framework for the rational design of drugs that modulate the activity of FGF, the crystal structure of complexes between bFGF and biologically active di- and trisaccharides (14) was determined (FIG. 3A). A view of a molecule of bFGF with bound Di-3 reveals four binding sites (FIG. 3B). Similar observations were made with the Tri-3/bFGF complex (FIG. 3, C and D). Bound- and apo-FGF structures superimpose with a root-mean-square deviation in $C^\alpha$ positions of 0.26 Å. It is therefore unlikely that a conformational change in FGF is involved in its mechanism of activation by heparin.

Figure 3C:
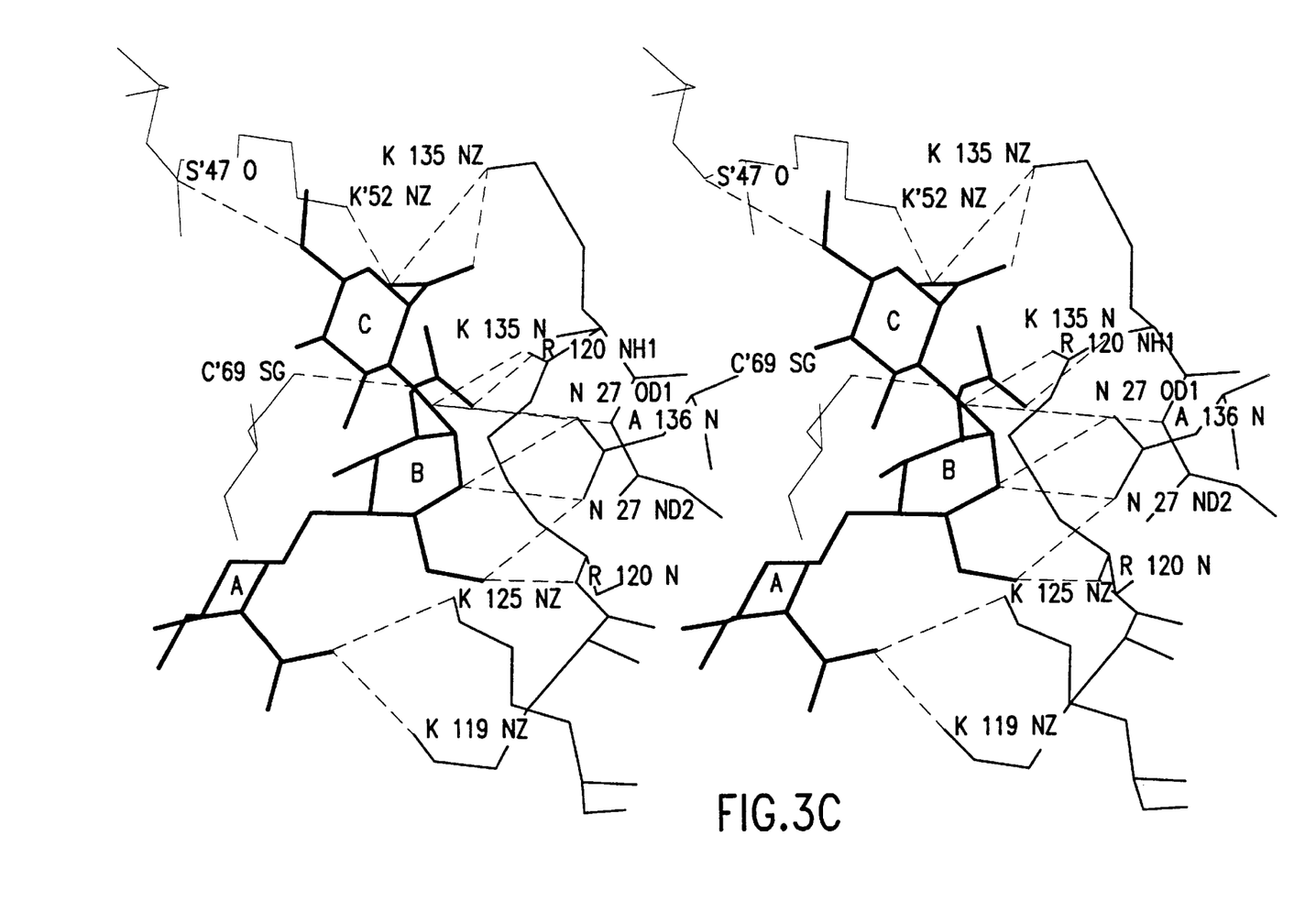
FIG. 3C: Stereodiagram of sites 1 and 1' with the Tri-3 ligand at a dimer interface.

Two ligand molecules were observed in the crystal structure. Each ligand contacted two symmetry-related FGF molecules thus defining two pairs of binding sites: 1, 1' and 2, 2' (FIG. 3B). Site 1 is similar to that observed for SOS bound to aFGF (15) and is also the site where sulfate ions are located in the bFGF apo-structure (16–18). Twelve hydrogen bonds, as defined in (19), form between FGF and Tri-3 at site 1. In comparison, only three hydrogen bonds form at site 1' (FIG. 3C). These data suggest that sites 1 and 1' are not equivalent in terms of binding affinity and therefore are unlikely to be involved in FGF oligomerization. Site 1' most likely results from crystal packing forces.

Figure 3D:
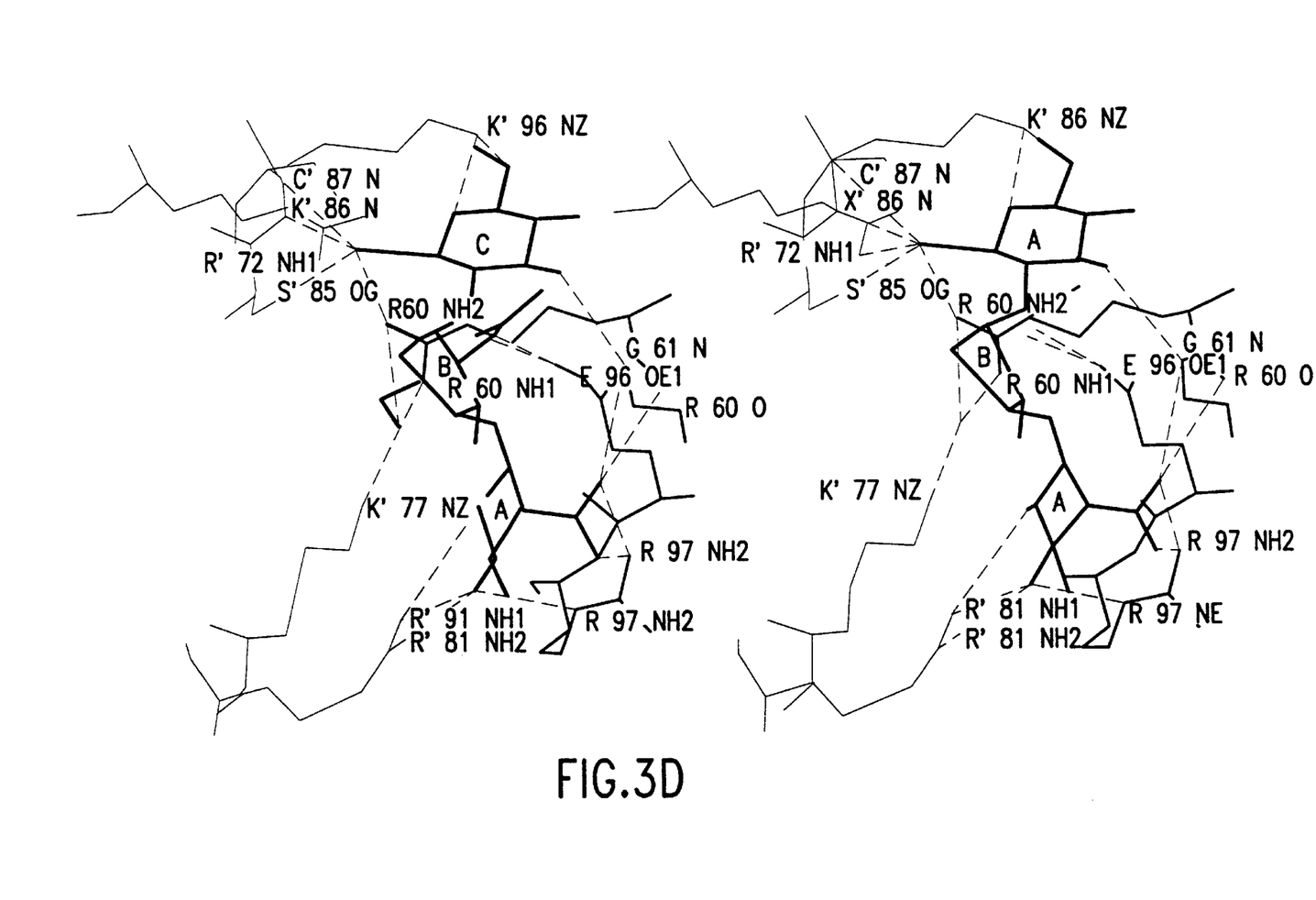
FIG. 3D: Stereodiagram of sites 2 and 2' with the Tri-3 ligand at a dimer interface.

Sites 2 and 2' (FIG. 3, B and D) have not been observed previously. This pair of sites is symmetry-related and consequently located very close to a crystal packing interface. In contrast to sites 1 and 1', both symmetry-related FGF molecules make extensive contact with Tri-3 at sites 2 (11 hydrogen bonds) and 2' (11 hydrogen bonds). Therefore, each of these sites is likely to bind ligand with high affinity and each can be considered an independent binding site. However, the average hydrogen bond length between Tri-3 and site 2' is 0.35 Å shorter than between Tri-3 and site 2.

In addition, when a more stringent definition of the hydrogen bond was used (20), eight hydrogen bonds were observed between Tri-3 and 2' compared to only four between Tri-3 and site 2. This indicates that site 2' may have greater affinity than site 2, for Tri-3. In the crystal structure, site 2 of one FGF molecule and site 2' of a symmetry-related FGF molecule are brought together by a single oligosaccharide molecule. Such contacts may be responsible for the oligomerization of FGF (see crosslinking experiments below).

Several other putative heparin/HS binding sites on bFGF have been suggested (21, 22); however, no density is observed at these sites for either Di-3 or Tri-3. In contrast to SOS, which has minimal biological activity and occupies a single site on the aFGF molecule, multiple binding sites for Di-3 and Tri-3 are observed. The capability of di- and trisaccharides to bind several sites on FGF may be a requirement for activity. Additionally, these sites may represent a path followed by heparin/HS polysaccharides between two FGF molecules complexed in a functional dimer.

The biological relevance of the potential dimer interface at site 2/2' is of significant interest since crosslinking studies demonstrate that di- and trisaccharides can induce FGF oligomerization. It is believed that inhibition of the FGF receptor dimerization (FIG. 6) can significantly influence the activity of FGF which, in turn, can be useful in cancer therapy.

Figure 4:
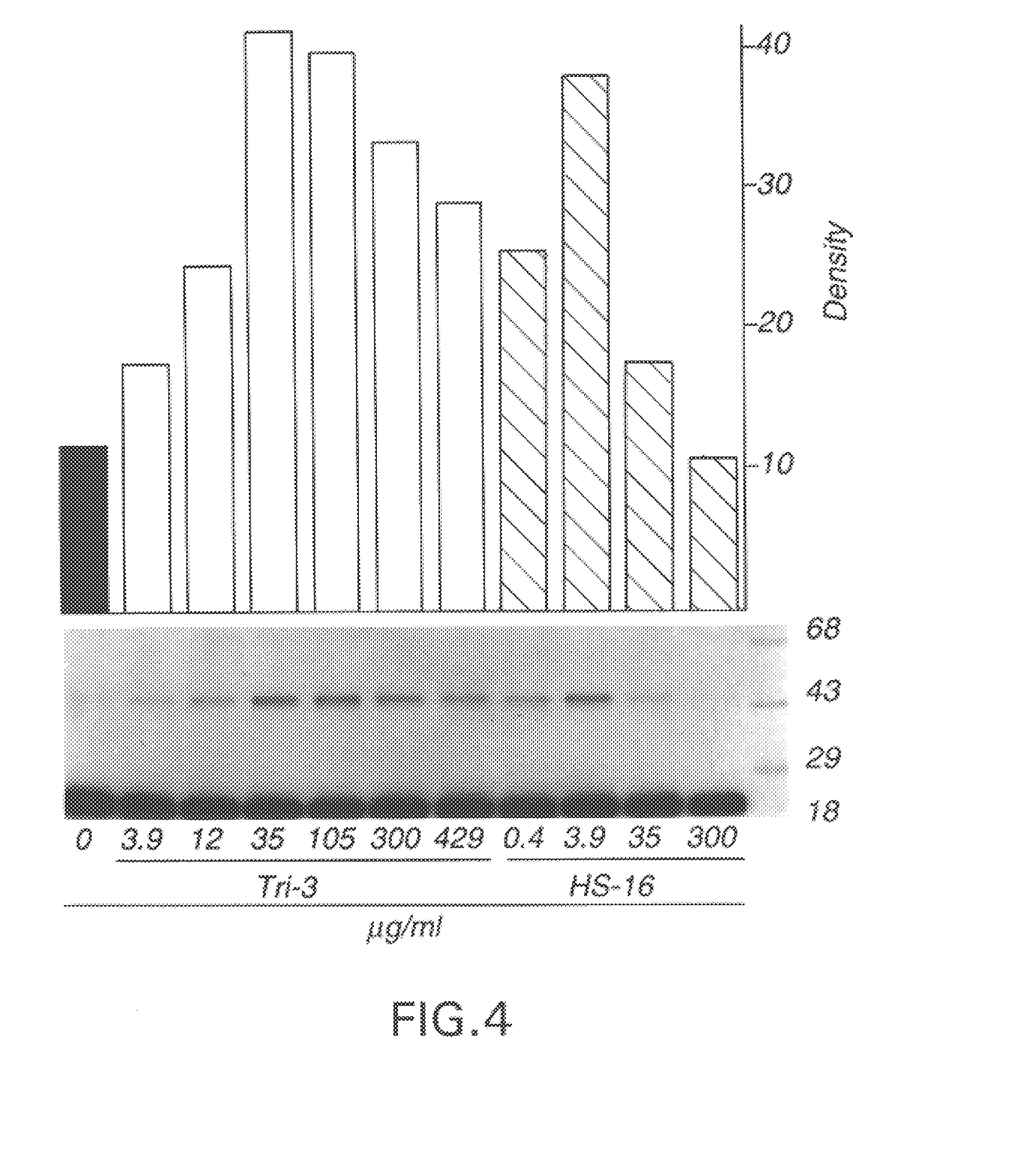

Di-3 and Tri-3, like the highly sulfated heparin hexadecasaccharide (HS-16), can induce FGF dimers as well as higher order oligomers (FIG. 4) (3). However, there are notable differences between the synthetic oligosaccharides and HS-16. The optimal concentration for dimerization activity induced by Tri-3 (35 µg/ml) is approximately 10-fold greater than that of HS-16 (3.9 µg/ml)

At concentrations 10- to 20-fold greater than these levels, the amount of dimerization seen with the hexadecasaccharide approaches basal levels. However, the amount of dimerization seen with the di- (13) or trisaccharide (FIG. 4) remains elevated. High ratios of HS-16 to FGF may favor a stoichiometry of several heparin oligosaccharides per FGF. Under these conditions, FGF dimerization may be inhibited sterically by the relatively large heparin molecule (HS-16). High ratios of di- or tri-saccharide to FGF would not be expected to sterically inhibit FGF dimerization.

Figure 6:
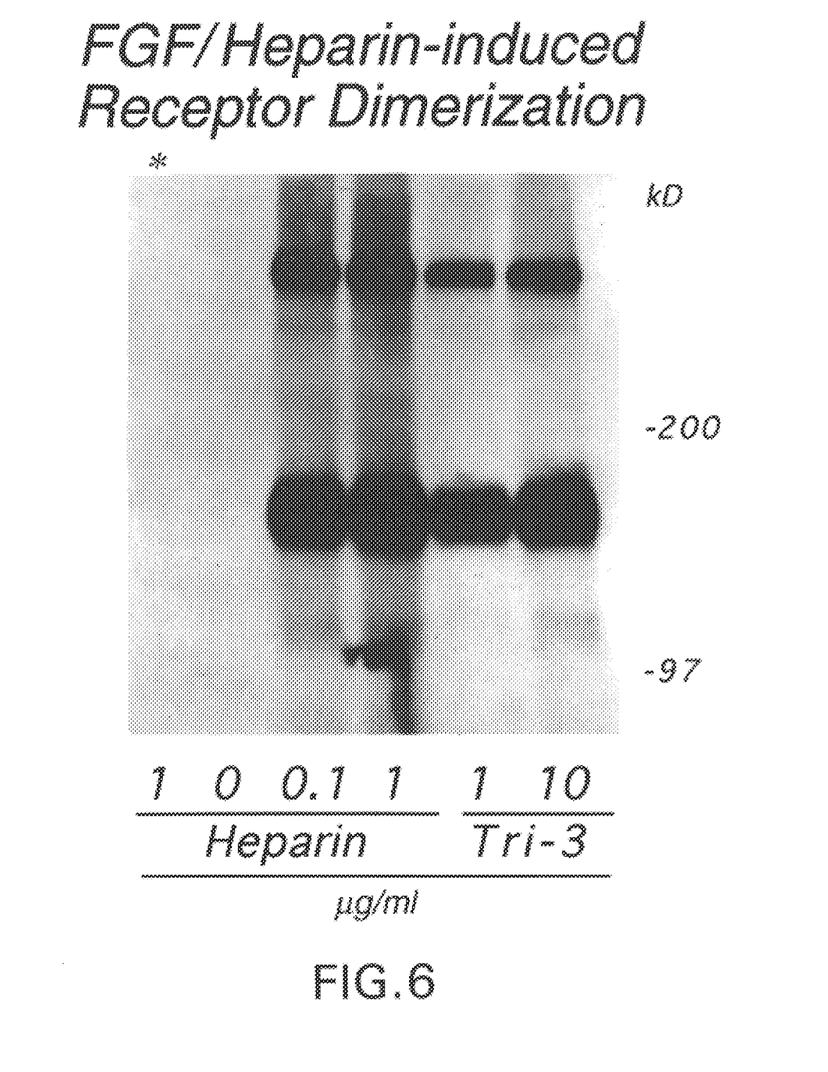

The dimerization of FGF receptors induced by FGF-2 and heparin-trisaccharide (Tri-3) is shown in FIG. 6. $^{125}$I-bFGF ($2\times10^6$ cpm) was incubated with $4\times10^6$ BaF3 -FGFR1 cells. Binding media (DMEM/0.1% BSA) was supplemented with the indicated concentration of heparin or Tri-3. (*) 200 ng/ml unlabeled FGF-2 added to binding media; Cells were washed once with the same media used for binding, and once with PBS. Crosslinking was as described previously (27).

Crosslinked receptors were electrophoresed on a 5% SDS polyacrylamide gel under reducing condition, and visualized by autoradiography. The lower band corresponds to receptor monomers crosslinked to FGF-2. The upper band corresponds to receptor dimers crosslinked to each other and to FGF-2.

The data presented here demonstrate that both non-sulfated di- and trisaccharides are biologically active in several FGF-dependent assays and suggest that FGF can specifically recognize structural features of the non-sulfated carbohydrate backbone of heparin/HS, independent of ionic interactions with highly charged sulfate groups. However, because heparin is more active than low-sulfated heparin (4), it is likely that ionic interactions could further stabilize this interaction. The lack of activity of Tri-2, a compound that only differs from Tri-3 (the most active compound tested) in having a N-sulfate group on the glucosamine residue, suggests that N-sulfated regions of heparin/HS may not be involved in FGFR activation.

Substitution of an N-sulfate in the Tri-3/bFGF crystal structure demonstrates repulsive interactions between the sulfate group and glutamic acid 96 in site 2.

Several studies demonstrate that 2-O-linked sulfate groups on the hexuronic acid residues of heparin/HS may be important for optimal activity (23–26).

Sulfation of our synthetic oligosaccharides at the 2-O position may further increase their affinity for bFGF and their biological activity.

The small size of the synthetic heparin/HS molecules suggests that linkage of multiple FGFs by heparin/HS in a "beads on a string model" is not an essential component of the mechanism of FGFR activation. A mechanism is suggested herein in which heparin/HS induces FGF dimers which in turn form stable complexes with FGF receptor molecules facilitating receptor dimerization. Recent binding studies, with the use of distinct members of the FGF family, suggest that an FGFR may contain multiple, partially overlapping binding sites that involve both immunoglobulin-like domains II and III (27). These data are consistent with FGFR molecules interacting with homo- or heterodimers of FGF.

TABLE 2

| | Glycosaminoglycan cofactor activity. | |
| --- | --- | --- |
| | Mitogenic activity‡ | bFGF binding* |
| heparin | 1.0 ± 0.5 | 1.0 |
| Di-2 | 69.5 ± 9.6 | >1340.6 |
| Di-3 | 26.0 | 1224.5 |
| Di-4 | 24.7 | 1224.5 |
| Di-5 | 463.6 | >1340.6 |
| Tri-1 | 1.2 ± 0.2 | 169.3 |
| Tri-2 | 470.6 ± 25.6 | >1340.6 |

TABLE 2-continued

| | Glycosaminoglycan cofactor activity. | |
| --- | --- | --- |
| | Mitogenic activity‡ | bFGF binding* |
| Tri-3 | 3.2 | 84.1 |
| SOS | 1380.8 ± 30.6 | 1340.6 |

‡Relative concentration (wt/vol.) required to incorporate $2 \times 10^4$ cpm $^3$H-thymidine into F32 cell DNA (3), ± standard deviation.
*Relative affinity (based on IC50 values (wt/vol.)) for heparin binding to bFGF.
Calculations based on molecular weights give similar ratios, assuming that the average molecular weight for heparin is 16,000 and that there are 15 FGF binding sites per heparin/HS molecule (29).

Various other examples will be apparent to the person skilled in the art after reading the present disclosure without departing from the spirit and scope of the invention. It is intended that all such other examples be included within the scope of the appended claims.

REFERENCES AND NOTES

1. C. Basilico and D. Moscatelli, *Adv. Cancer Res.* 59, 115 (1992).

2. M. Klagsbrun and A. Baird, *Cell* 67,229 (1991).

3. D. M. Ornitz et al., *Mol. Cel. Biol.* 12,240 (1992).

4. A. Yayon, M. Klagsbrun, J. D. Esko, P. Leder, D. M. Omitz, *Cell* 64,841 (1991).

5. A. C. Rapraeger, A. Krufka, B. B. Olwin, *Science* 252,1705 (1991).

6. M. Kan et al., *Science* 259, 1918 (1993).

7. M. Ishihara et al., *J. Biol. Chem.* 268, 4675 (1993).

8. B. Casu, Structure of heparin and heparin fragments. In *Heparin and related polyshacchardies: Structure and activities.*, F. A. Ofosu, I. Danishefsky, J. Hirsh, Eds. (New York Academy of Sciences, New York, 1989), vol. 556, pp. 1.

9. J. Westman, M. Nilsson, D. M. Ornitz, C. -M. Svahn, *J. Carbohydrate Chem.* 14, pp 95–113 (January 1995).

10. J. Folkman et al., *Ann. Surg.* 214, 414 (1991).

11. D. Moscatelli, *J. Cell. Phys.* 131, 123 (1987).

12. Heparin iodination was as in (30). Heparin binding to FGF was determined by incubating 4 nM FGF with $^{125}$I-heparin and competitor polysaccharide. Complexes were immunoprecipitated with 1:250 dilutions of monoclonal antibody DG2 (for bFGF) or a polyclonal antibody (for aFGF), and protein A sepharose (Sigma). Washing and quantitation was as previously described for soluble receptor binding assays (3).

13. D. M. Ornitz, unpublished data.

14. Small crystals of complexes of bFGF (25 mg/ml) and Di-3 or Tri-3 (1 to 13 ratios) were obtained at 20° C. (33) in 15% or 17.5% (w/v), respectively, polyethylene glycol (average Mr=3350), 0.1M Hepes (pH 6.8), and subsequently macroseeded repeatedly in fresh drops of the same solution. Both complexes form triclinic crystals with one molecule in the asymmetric unit (a=30.9, b=33.3, c=34.7, α=87.6, β=85.4, γ=76.4). Structure determination was carried out as in (34, 35) with the model generated by (18). The oriented model was then refined by simulated annealing and least-squares optimization, as in (37). Data from 40 Å to 2.2 Å were used. Examination of a map generated using the coefficients (|Fo|−|Fc|)exp(−iα$_c$) showed density that could accommodate saccharide molecules in both sites 1 and 2. Subsequent incorporation of the structure factor of the solvent resulted in improved density. Model building and correction was carried out with the programs O (38, 39) and turbo (40). Least-squares refinement of the saccharide-FGF structure was carried out with X-PLOR (36), with stereochemical parameters for Di-3 and Tri-3 taken from the topology and parameter files provided for pyranoside sugars by the X-PLCR package (36). The final R-factor is 22.0% and 22.8% for the Tri-3/bFGF and Di-3/bFGF structures, respectively, with good stereochemistry. Analysis of the temperature factors indicated that the occupancy of the saccharides is likely to be partial. Occupancy of the di- and trisaccharide was set to 0.5, which results in temperature factors that are comparable to those for side-chains observed to coordinate the ligands.

15. D Zhu, B. T. Hsu, D. C. Rees, *Structure* 1, 27 (1993).

16. J. Zhang, L. S. Cousens, P. J. Barr, S. R Sprang, *Proc. Natl. Acad. Sci. U.S.A.* 88,3446 (1991).

17. X. Zhu et al., *Science* 251,90 (1990).

18. A. E Eriksson, L. S. Cousens, L. H. Weaver, B. W. Matthews, *Proc. Natl. Acad. Sci. U.S.A.* 88, 3441 (1991).

19. I. K. McDonald and J. M. Thornton, *J. Mol. Biol.* 238,777 (1994).

20. E. N. Baker and R. E. Hubbard, *Prog. Biophys. Mol. Bio.* 44,97 (1984).

21. A. Baird, D. Schubert, N. Ling, R. Guillemin, *Proc. Natl. Acad. Sci. U.S.A.* 85,2324 (1988).

22 W. F. Heath, A. S. Cantrell, N. G. Mayne, S. R Jaskunas, *Biochemistry* 30,5608 (1991).

23. S. Guimond, M. Maccarana, B. B. Olwin, U. Lindahl, A. C Rapraeger, *J. Biol. Chem.* 268, 23906 (1993).

24. M. Maccarana, B. Casu, U. Lindahl, *J. Biol. Chem.* 268,23898 (1993).

25. H. Habuchi et al., *Biochem. J.* 285,805 (1992).

26. D. Aviezer et al., *J. Biol. Chem.* 269, 114 (1994).

27. A. T. Chellaiah, D. G. McEwen, S. Werner, J. Xu, D. M. Ornitz, *J. Biol. Chem.* 269, 11620 (1994).

28. C. Svahn, A. Ansari, T. Wehler, unpublished data.

29. H. Mach et al, *Biochemistry* 32,5480 (1993).

30. C. G. Glabe, P. K. Harty, S. D. Rosen, *Anal. Biochem.* 130,287 (1983).

31. L. W. Burrus and B. B. Olwin, *J. Biol. Chem.* 264, 18647 (1989).

32. P. J. Kraulis, *J. Appl. Crystallogr.* 24, 946 (1991).

33. A. McPherson, *Eur. J. Biochem.* 189, 1 (1990).

34. M. G. Rossmann, The molecular replacement method. In *International Scientific Review Series*(Gordon and Breach, New York, 1972), vol. 13,.

35. A. T. Brunger, *Acta Crystallogr.* 46,46 (1990).

36. A. T. Brunger, *X-PLOR Manual, Version* 3.1. (Yale University, New Haven, Conn., 1992).

37. W. I. Weis, A. T. Brunger, J. J. Skehel, D. C. Wiley, *J. Molec. Biol.* 212,737 (1990).

38. T. A. Jones and S. Thirup, *EMBO J.* 5, 819 (1986).

39. T. A. Jones, J. Y. Zou, S. W. Cowan, M. Kjeldgaard, *Acta Crystallogr.* 47,110 (1991).

40. A. Roussel and C. Camblllau, TURBO-FRODO. In *Silicon Graphics Geometry Partners Directory*(Silicon Graphics, 1991) pp. 86.

41. We thank D. McEwen and S. Mathews for discussion, A. Chellaiah, T. Opera, J. Xu and M. Weurffel for help. bFGF and antibody DG2 were gifts from J. Abraham (Scious Nova) and W. Herblin (DuPont/Merk), respectively. aFGF and anti-aFGF antisera was a gift from K. Thomas (Merck). Fluoresceinated heparin was a gift from C. Parish (Australian National University, Canberra, Australia). SOS was from Bukh Meditec. Heparin was from Hepar Inc. This work was supported in part by grants from the NIH (CA60673), Monsanto-Searle, and Washington University Medical School.

What is claimed is:

1. The method for identifying a small molecular weight compound which is up to about 1000 Daltons that interacts with FGF to thereby modulate its activity comprising subjecting said compound to assay by one or more of the following procedures:

(a) testing the ability of the compound as a modulator of FGF-dependent mitogenesis on FGF receptor expressing cells and comparing against the mitogenic activity of heparin or sucrose octasulfate;

(b) testing the ability of the compound to compete with the binding of $^{125}$I-heparin to FGF;

(c) testing the ability of the compound to enhance or inhibit the binding of FGF to a soluble or cell surface FGF receptor;

(d) testing the ability of the compound to enhance or inhibit FGF dimerization;

(e) testing the ability of the compound to enhance or inhibit FGF receptor dimerization; and (f) testing the ability of the compound to enhance or inhibit FGF binding to heparin or heparin immobilized on a gel matrix.

2. The method of claim 1 in which the FGF is bFGF.

3. The method of claim 1 in which the FGF is aFGF.

4. The method of claim 1 in which the FGF receptor is the FGF receptor-1.

5. The method of claim 1 in which the compound tested is an oligosaccharide having from 2 to about 6 saccharide units.

* * * * *